(12) United States Patent
Lin et al.

(10) Patent No.: US 8,573,663 B1
(45) Date of Patent: Nov. 5, 2013

(54) FINGER-GESTICULATION HAND DEVICE

(75) Inventors: Rong-Bin Lin, Taichung (TW);
Ying-Lung Lin, Taichung (TW); Bo-Yi Chou, Taichung (TW); Che-Hau Wu, Taichung (TW)

(73) Assignee: Precision Machinery Research & Development Center, Taichung (TW)

( * ) Notice: Subject to any disclaimer, the term of this patent is extended or adjusted under 35 U.S.C. 154(b) by 0 days.

(21) Appl. No.: 13/459,471

(22) Filed: Apr. 30, 2012

(51) Int. Cl.
*B25J 15/10* (2006.01)

(52) U.S. Cl.
USPC .......................................... 294/111; 294/106

(58) Field of Classification Search
USPC ................ 294/106, 111, 200, 213; 623/64; 901/36, 38, 39
See application file for complete search history.

(56) References Cited

U.S. PATENT DOCUMENTS

| | | | |
|---|---|---|---|
| 2,567,066 A * | 9/1951 | Goldman | 623/24 |
| 3,866,966 A * | 2/1975 | Skinner, II | 294/106 |
| 4,074,444 A * | 2/1978 | Laenger et al. | 434/112 |
| 4,246,661 A * | 1/1981 | Pinson | 623/25 |
| 4,378,215 A * | 3/1983 | Sparks | 434/113 |
| 5,080,681 A * | 1/1992 | Erb | 623/63 |
| 5,080,682 A * | 1/1992 | Schectman | 623/64 |
| 5,092,646 A * | 3/1992 | Smallridge | 294/111 |
| 5,200,679 A * | 4/1993 | Graham | 318/568.16 |
| 6,817,641 B1 * | 11/2004 | Singleton, Jr. | 294/106 |
| 6,896,704 B1 * | 5/2005 | Higuchi et al. | 623/64 |
| 2006/0145495 A1 * | 7/2006 | Fang et al. | 294/106 |
| 2011/0040408 A1 * | 2/2011 | De La Rosa Tames et al. | 700/258 |

* cited by examiner

*Primary Examiner* — Dean Kramer
(74) *Attorney, Agent, or Firm* — Fish & Richardson P.C.

(57) ABSTRACT

A finger-gesticulation hand device includes a base frame representing a metacarpal part of the human hand, and at least three digits mounted on the base frame and appearing to be a thumb and at least two fingers. Each digit has at least two phalange portions respectively linked by two joints which permit a flexing movement of the phalange portions between extended and flexed positions. An actuating cord passes through each digit and is actuated by a solenoid actuator unit to pull the phalange portions of the respective digit to the flexed position. The hand device is simple in construction and capable of making hand gestures in a simple manner.

6 Claims, 7 Drawing Sheets

FINGER-GESTICULATION HAND DEVICE

BACKGROUND OF THE INVENTION

1. Field of the Invention

This invention relates to a hand device, more particularly to a finger-gesticulation hand device.

2. Description of the Related Art

A conventional multi-fingered robot hand, such as those disclosed in U.S. Pat. Nos. 8,100,451 B2 and 7,735,887 B2, is capable of making motions similar to human hand motions, like grasping articles, making hand gestures, etc. To make complicated hand motions and provide a sufficient grasping force, the conventional robot hand is provided with five digit mechanisms, each having three bending joints which are actuated by an individual drive unit. Such joints and drive units are complicated in construction.

SUMMARY OF THE INVENTION

An object of the present invention is to provide a finger-gesticulation hand device which is simple in structure and which can be manufactured at a relatively low cost.

According to this invention, the finger-gesticulation hand device includes a base frame having a major wall which represents a metacarpal part of the human hand and which defines an upright plane, and at least three digits appearing to be a thumb and at least two fingers. Each of the digits has a metacarpal portion which is mounted on the major wall, a proximate-and-intermediate phalange portion which is linked to the metacarpal portion by a first joint that is disposed to permit turning of the proximate-and-intermediate phalange portion relative to the metacarpal portion between flexed and extended positions, a first biasing member which is disposed to bias the proximate-and-intermediate phalange portion toward the extended position, a distal phalange portion which is linked to the proximate-and-intermediate phalange portion by a second joint that is disposed to permit turning of the distal phalange portion relative to the proximate-and-intermediate phalange portion between flexed and extended positions, and a second biasing member which is disposed to bias the distal phalange portion toward the extended position. Each of at least three actuating cords has a first end secured to the distal phalange portion of a respective one of the digits, and passes through the proximate-and-intermediate phalange portion and the metacarpal portion to terminate at a second end that is disposed adjacent to the base frame. A first solenoid actuator unit is disposed on the base frame, and has a first solenoid member and a first plunger to which the second end of one of the actuating cords is fastened. The first plunger is coupled with the first solenoid member such that, when the first plunger is activated to move to an activated position, the distal and proximate-and-intermediate phalange portions of a corresponding one of the digits representing the thumb are pulled to be displaced to the flexed positions. A second solenoid actuator unit is disposed on the base frame, and has a second solenoid member and a second plunger to which the second ends of the other two of the actuating cords are fastened. The second plunger is coupled with the second solenoid member such that, when the second plunger is activated to move to an activated position, the distal and proximate-and-intermediate phalange portions of the corresponding ones of the digits representing the fingers are pulled to be displaced to the flexed positions.

BRIEF DESCRIPTION OF THE DRAWINGS

Other features and advantages of the present invention will become apparent in the following detailed description of the preferred embodiment of the invention, with reference to the accompanying drawings, in which.

DETAILED DESCRIPTION OF THE PREFERRED EMBODIMENT

Figure 1:
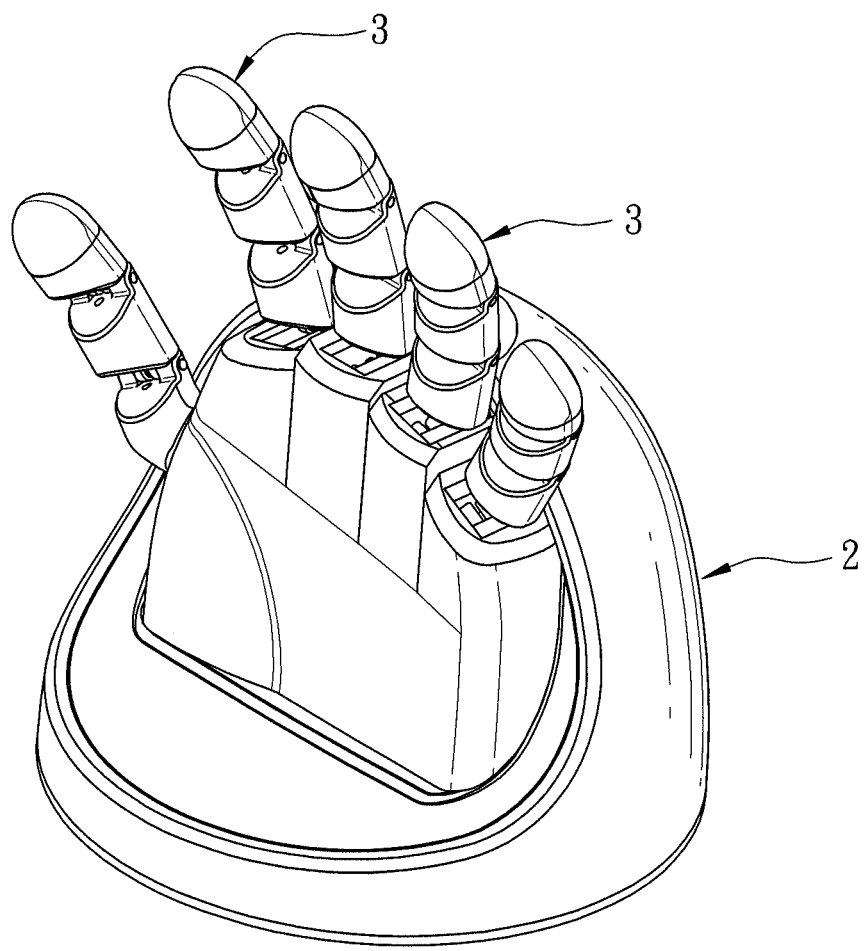
FIG. 1 is a perspective view of the preferred embodiment of a finger-gesticulation hand device according to this invention when making a gesture "paper" as in a hand game.
Figure 2:
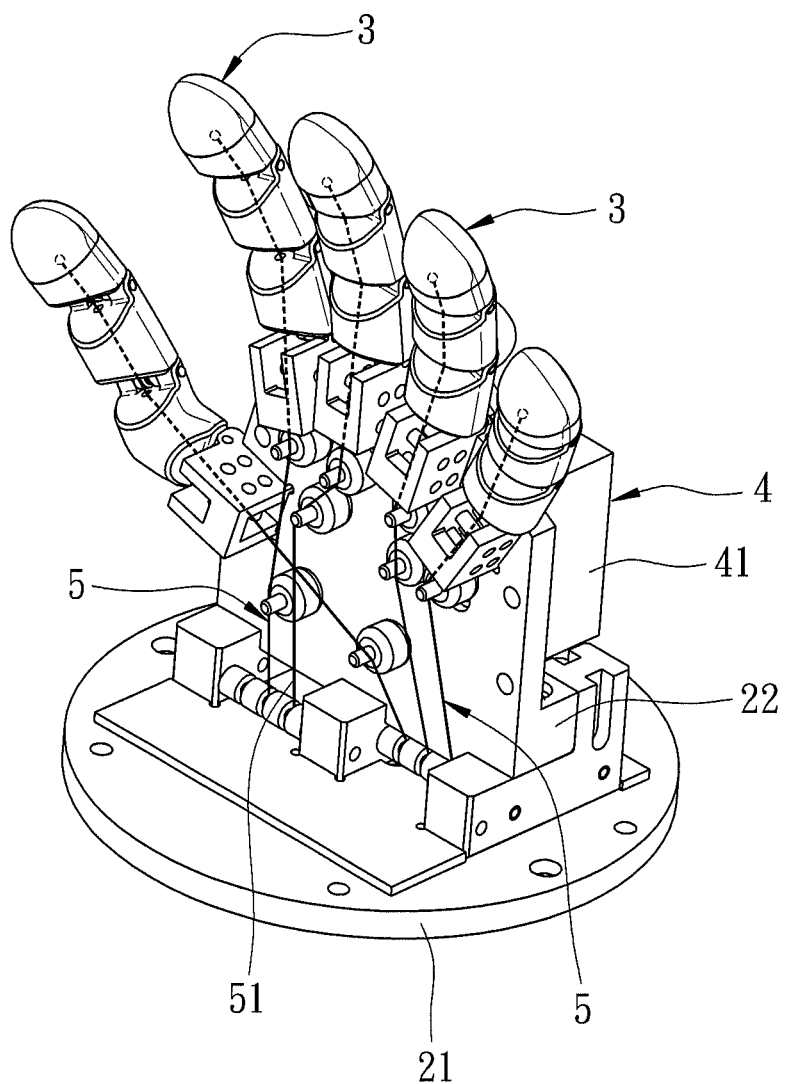
FIG. 2 is a perspective view showing interior components of the preferred embodiment.
Figure 3:
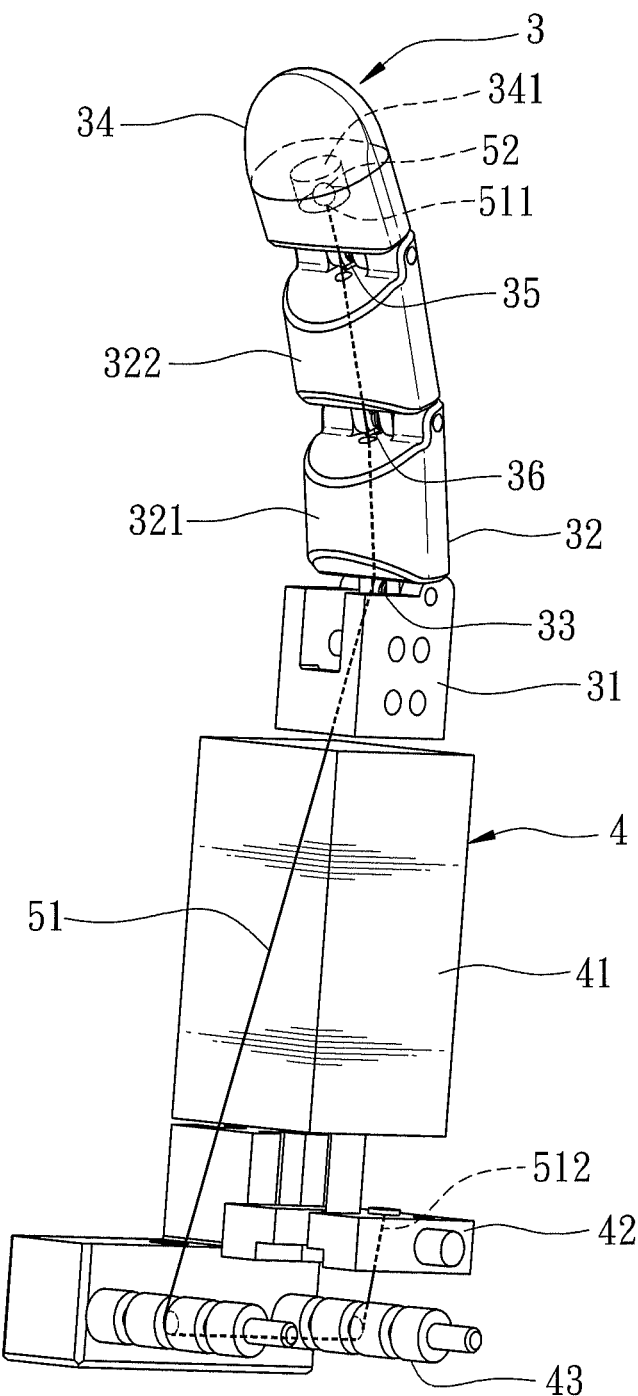
FIG. 3 is a perspective view of a digit assembly of the preferred embodiment in an extended state.

Referring to FIGS. 1 to 3, the preferred embodiment of a finger-gesticulation hand device according to the present invention is shown to comprise a base frame 2, five digits 3, five actuating units 5, and first and second solenoid actuator units 4.

The base frame 2 has a base seat 21 and a major wall 22 which represents a metacarpal part of the human hand and which extends uprightly from the base seat 21 to define an upright plane.

Figure 4:
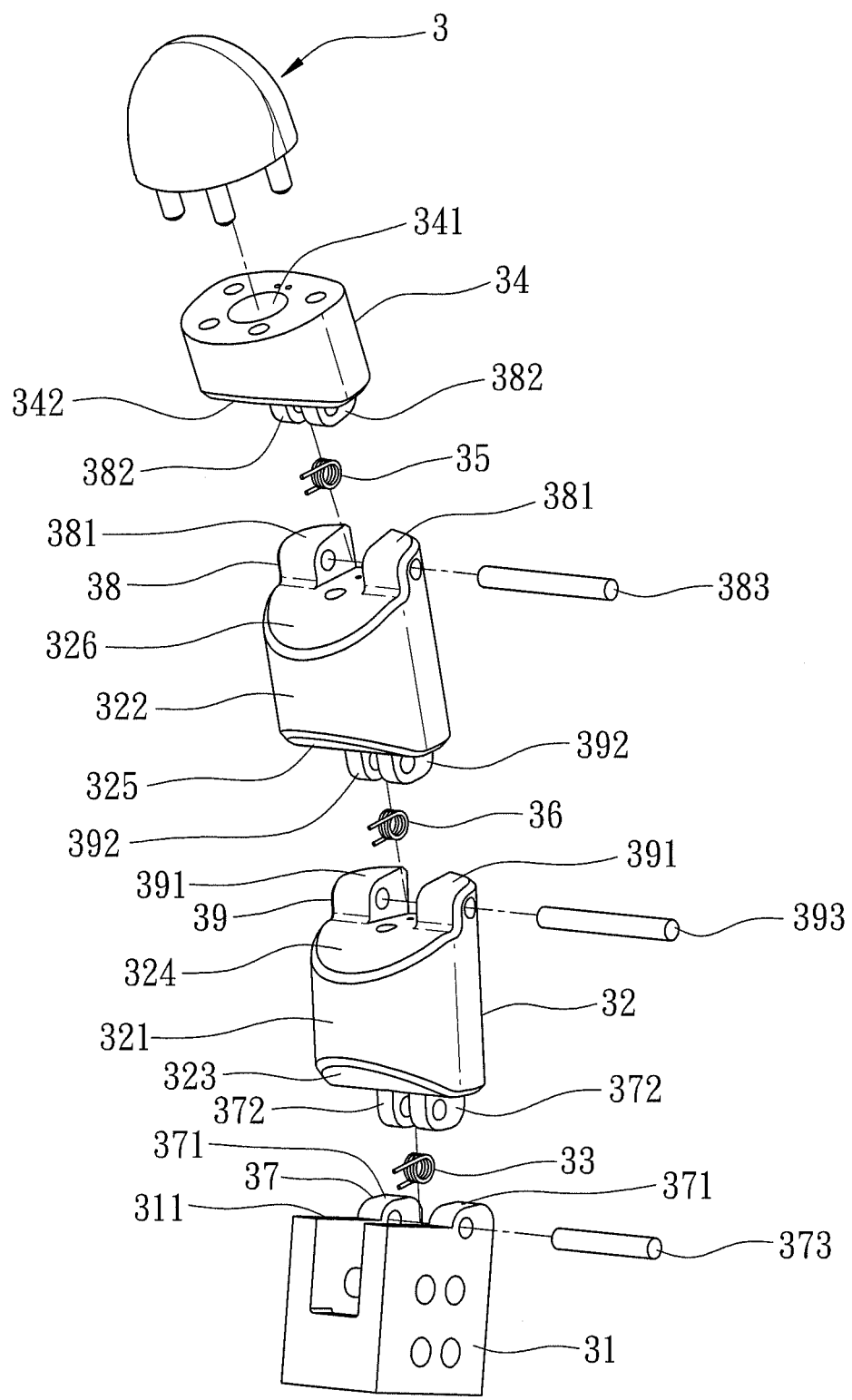
FIG. 4 is an exploded perspective view of the digit assembly.

Referring to FIGS. 2 to 4, the digits 3 appear to be a thumb and four fingers, respectively. Each of the digits 3 has a metacarpal portion 31 which is mounted on the major wall 22, a proximate-and-intermediate phalange portion 32 which is linked to the metacarpal portion 31 by a first joint 37 that is disposed to permit turning of the proximate-and-intermediate phalange portion 32 relative to the metacarpal portion 31 between flexed and extended positions, a first biasing member 33 which is disposed to bias the proximate-and-intermediate phalange portion 32 toward the extended position, a distal phalange portion 34 which is linked to the proximate-and-intermediate phalange portion 32 by a second joint 38 that is disposed to permit turning of the distal phalange portion 34 relative to the proximate-and-intermediate phalange portion 32 between flexed and extended positions, and a second biasing member 35 which is disposed to bias the distal phalange portion 34 toward the extended position. The metacarpal and distal phalange portions 31, 34 of each digit 3 respectively have first and second flat end surfaces 311, 342 adjacent to the proximate-and-intermediate phalange portion 32. The distal phalange portion 34 of each digit 3 has a through hole 341.

The proximate-and-intermediate phalange portion 32 of each digit 3 includes proximate and intermediate phalange segments 321, 322 which are respectively linked to the metacarpal and distal phalange portions 31, 34, and which are linked to each other by a third joint 39 that is disposed to permit turning of the intermediate phalange segment 322 relative to the proximate phalange segment 321 between flexed and extended positions. Each digit 3 further includes a third biasing member 36 disposed to bias the intermediate phalange segment 322 toward the extended position.

In particular, the proximate phalange segment 321 has a first inclined end surface 323 facing the first flat end surface 311, and an opposite second inclined end surface 324. The intermediate phalange segment 322 has a third inclined end surface 325 facing the second inclined end surface 324, and an opposite fourth inclined end surface 326 facing the second flat end surface 342 of the distal phalange portion 34.

Each of the first, second and third joints 37, 38, 39 includes a pair of outer lugs 371, 381, 391 which are disposed on the end surface 311, 326, 324 of a respective one of the metacarpal portion 31, and the intermediate and proximate phalange segments 322, 321, a pair of inner lugs 372, 382, 392 which are disposed on the end surface 323, 342, 325 of a corresponding one of the proximate phalange segment 321, the distal phalange portion 34, and the intermediate phalange segment 322 and which are juxtaposed with the outer lugs 371, 381, 391, and a hinge pin 373, 383, 393 which is led through the inner lugs 372, 382, 392 and journalled on the outer lugs 371, 381, 391. By virtue of the inclined end surfaces 323, 324, 325, 326 which are configured to be divergent from the corresponding hinge pins 373, 393, 383, respectively, more leeway can be provided for a flexing movement of the corresponding one of the proximate and intermediate phalange segments 321, 322 and the distal phalange portion 34.

Each of the first, second and third biasing members 33, 35, 36 is a torsion spring which is sleeved on the hinge pin 373, 383, 393 of a corresponding one of the first, second and third joints 37, 38, 39 and which has two ends that respectively abut against the end surfaces 311, 323; 326, 342; 324, 325 of two corresponding ones of the metacarpal portion 31, the proximate and intermediate phalange segments 321, 322 and the distal phalange portion 34.

Each of the actuating units 5 includes an actuating cord 51 disposed in the respective digit 3, and a head 52 connected to a first end 511 of the actuating cord 51 to be retainingly received in the through hole 341 in the distal phalange portion 34. The actuating cord 51 passes through the intermediate and proximate phalange segments 322, 321 and the metacarpal portion 31, and terminates at a second end 512 that is disposed adjacent to the base frame 2.

Figure 5:
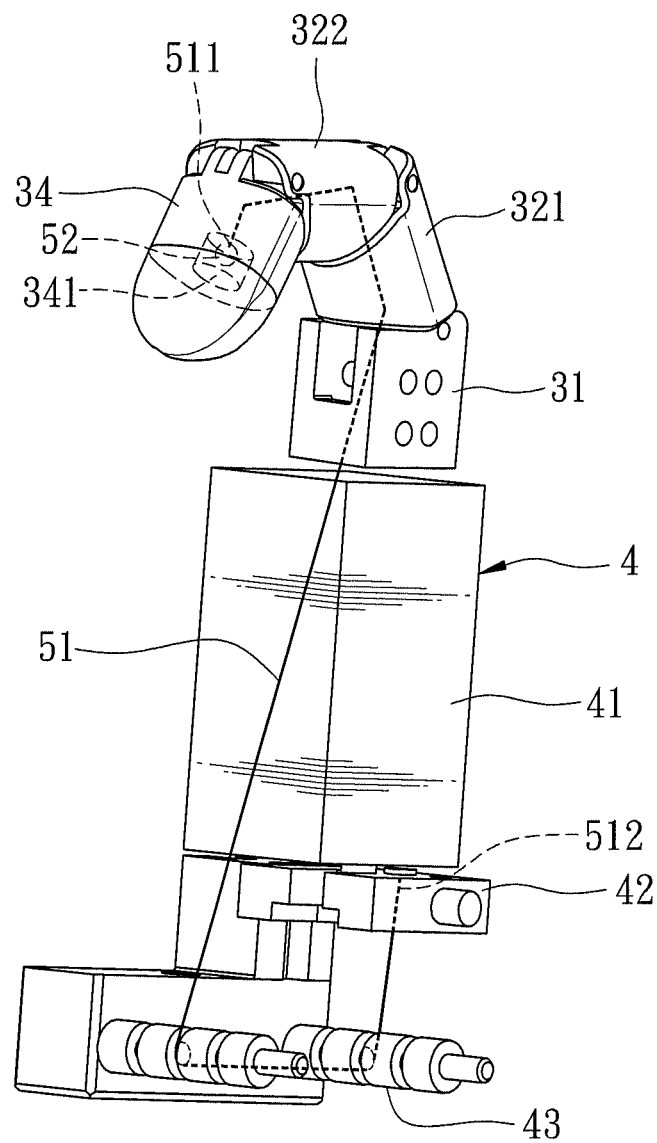
FIG. 5 is a perspective view of the digit assembly in a flexed position.
Figure 6:
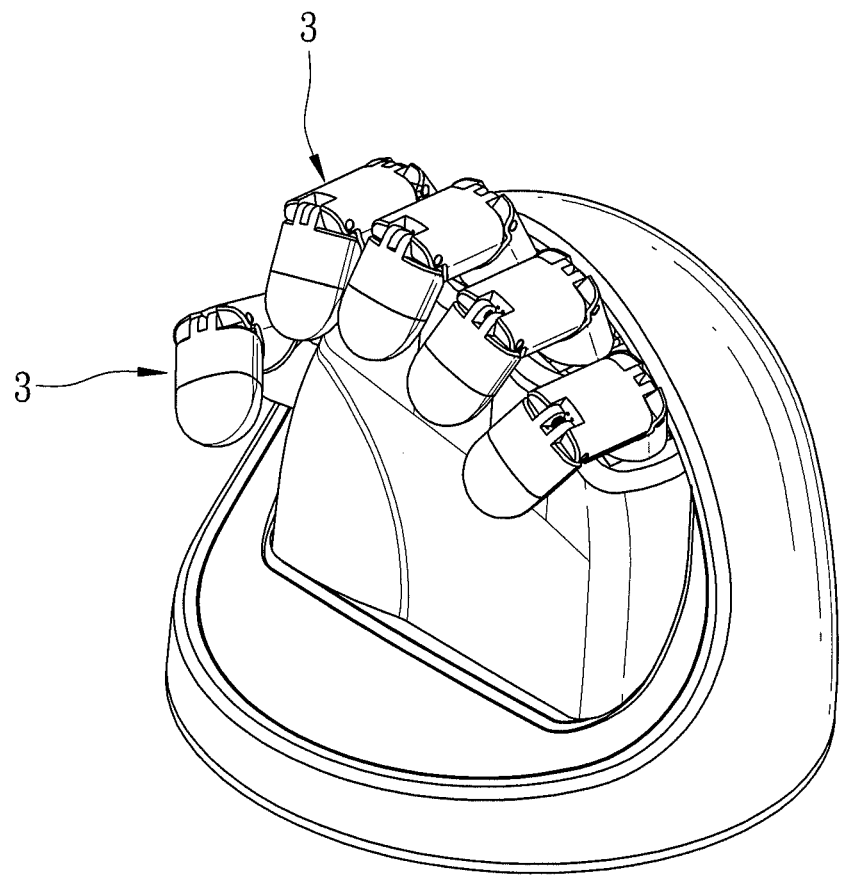
FIG. 6 is a perspective view of the preferred embodiment when making a gesture "rock" as in the hand game.
Figure 7:
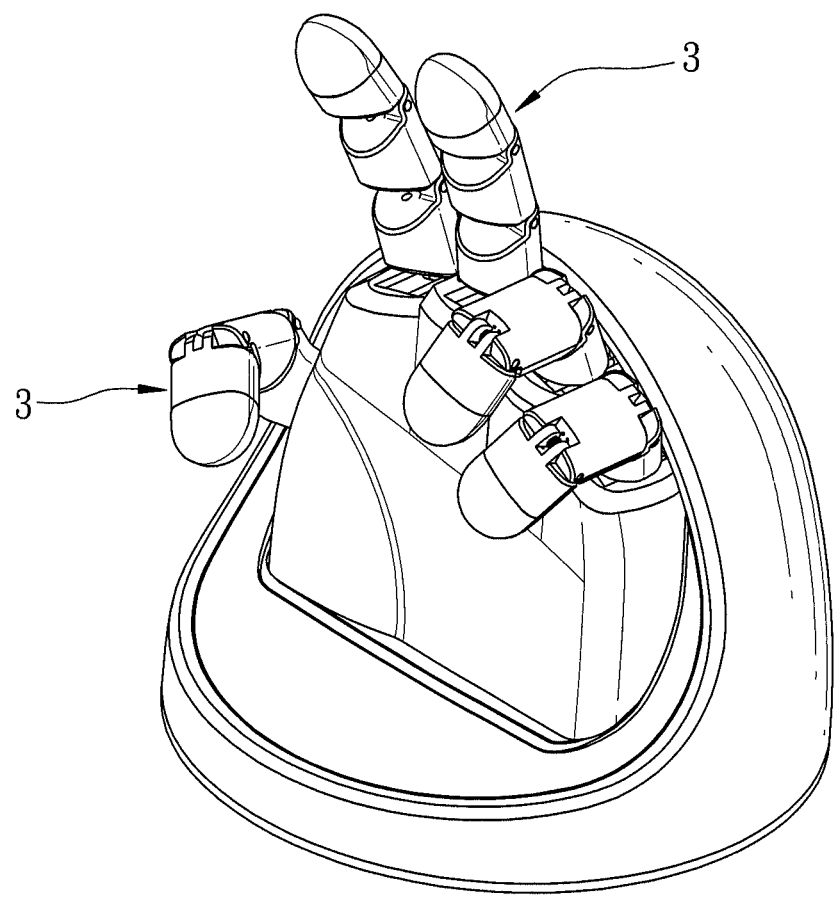
FIG. 7 is a perspective view of the preferred embodiment when making a gesture "scissors" as in the hand game.

The first solenoid actuator unit 4 is disposed on the base frame 2 to actuate three of the digits 3 representing the thumb and the ring and little fingers, and has a first solenoid member 41 and a first plunger 42 coupled with and activated by the first solenoid member 41. The three corresponding actuating cords 51 are wound on a first direction reversing member 43 that is mounted on the base seat 21 to permit the second ends 512 thereof to be tensely fastened to the first plunger 42. When the first plunger 42 is activated to move closer to the first solenoid member 41 to an activated position, as shown in FIG. 5, the distal and proximate-and-intermediate phalange portions 34, 32 of the corresponding digits 3 are pulled through the actuating cords 51 to be displaced to the flexed positions.

Similarly, the second solenoid actuator unit 4 is disposed on the base frame 2 to actuate two of the digits 3 representing the index and middle fingers, and has a second solenoid member 41 and a second plunger 42 coupled with and activated by the second solenoid member 41. The two corresponding actuating cords 51 are wound on a second direction reversing member 43 that is mounted on the base seat 21 to permit the second ends 512 thereof to be tensely fastened to the second plunger 42. When the second plunger 42 is activated by electromagnetic attraction to move closer to the second solenoid member 41 to an activated position, as shown in FIG. 5, the distal and proximate-and-intermediate phalange portions 34, 32 of the corresponding digits 3 are pulled through the actuating cords 51 to be displaced to the flexed positions.

Referring to FIGS. 1, 2, 6 and 7, in this embodiment, the finger-gesticulation hand device can be actuated to make expressive gestures "rock," "paper," or "scissors" as in "rock-paper-scissors."

As illustrated, by means of the first and second solenoid actuator units 4, and by virtue of the actuating cords 51 for pulling the individual digits 3, the hand device of this invention can be actuated to make hand gestures in a simple manner, and can be manufactured at a relatively low cost.

While the present invention has been described in connection with what is considered the most practical and preferred embodiment, it is understood that this invention is not limited to the disclosed embodiment but is intended to cover various arrangements included within the spirit and scope of the broadest interpretations and equivalent arrangements.

What is claimed is:

1. A finger-gesticulation hand device, comprising:
a base frame having a major wall which represents a metacarpal part of the human hand and which defines an upright plane;
five digits representing a thumb and four fingers of the human hand, each having a metacarpal portion which is mounted on said major wall, a proximate-and-intermediate phalange portion which is linked to said metacarpal portion by a first joint that is disposed to permit turning of said proximate-and-intermediate phalange portion relative to said metacarpal portion between flexed and extended positions, a first biasing member which is disposed to bias said proximate-and-intermediate phalange portion toward the extended position, a distal phalange portion which is linked to said proximate-and-intermediate phalange portion by a second joint that is disposed to permit turning of said distal phalange portion relative to said proximate-and-intermediate phalange portion between flexed and extended positions, and a second biasing member which is disposed to bias said distal phalange portion toward the extended position;
five actuating cords, each having a first end secured to said distal phalange portion of a respective one of said digits, and passing through said proximate-and-intermediate phalange portion and said metacarpal portion to terminate at a second end that is disposed adjacent to said base frame;
a first solenoid actuator unit disposed on said base frame, and having a first solenoid member and a first plunger to which said second ends of three of said actuating cords are fastened, said first plunger being coupled with said first solenoid member such that, when said first plunger is activated to move to an activated position, said distal and proximate-and-intermediate phalange portions of three corresponding ones of said digits which represent respectively the thumb and two of the fingers are pulled to be displaced to the flexed positions; and
a second solenoid actuator unit disposed on said base frame, and having a second solenoid member and a second plunger to which said second ends of the other two of said actuating cords are fastened, said second plunger being coupled with said second solenoid member such that, when said second plunger is activated to move to an activated position, said distal and proximate-and-intermediate phalange portions of the other two corresponding ones of said digits which represent respectively the other two of the fingers are pulled to be displaced to the flexed positions.

2. The finger-gesticulation hand device as claimed in claim 1, wherein each of said first and second solenoid actuator unit has a direction reversing member disposed on said base frame, each of said actuating cords is wound on said direction reversing member of a corresponding one of said first and second solenoid actuator units to permit said second end to be tensely fastened to a corresponding one of said first and second plungers, each of said first and second plungers being moved closer to a respective one of said first and second solenoid members to the activated position.

3. The finger-gesticulation hand device as claimed in claim 2, wherein said proximate-and-intermediate phalange portion of each of said digits includes proximate and intermediate phalange segments which are respectively linked to said metacarpal and distal phalange portions, and which are linked to each other by a third joint that is disposed to permit turning of said intermediate phalange segment relative to said proximate phalange segment between flexed and extended positions, each of said digits having a third biasing member which is disposed to bias said intermediate phalange segment toward the extended position.

4. The finger-gesticulation hand device as claimed in claim 3, wherein each of said first, second and third joints includes a pair of outer lugs which are disposed on an end surface of one of said metacarpal portion and said intermediate and proximate phalange segments, a pair of inner lugs which are disposed on an end surface of a corresponding one of said proximate phalange segment, said distal phalange portion and said intermediate phalange portion, and which are juxtaposed with said outer lugs, and a hinge pin which is led through said inner lugs and journalled on said outer lugs.

5. The finger-gesticulation hand device as claimed in claim 4, wherein each of said first, second and third biasing members is a torsion spring which is sleeved on said hinge pin of a corresponding one of said first, second and third joints and which has two ends that respectively abut against said end surfaces of two corresponding ones of said metacarpal portion, said proximate and intermediate phalange segments and said distal phalange portion.

6. The finger-gesticulation hand device as claimed in claim 5, wherein two opposing ones of said end surfaces at each of said first, second and third joints are configured to be divergent from a corresponding one of said hinge pins so as to provide more leeway for a flexing movement of the corresponding one of said proximate-and-intermediate and distal phalange portions.

* * * * *